United States Patent [19]

Sisto et al.

[11] Patent Number: 5,051,404
[45] Date of Patent: Sep. 24, 1991

[54] TRIPEPTIDE COMPOUNDS HAVING HYPOTENSIVE ACTIVITY

[75] Inventors: Alessandro Sisto, Rome; Antonio S. Verdini, Monterotondo; Antonino Virdia, Rome; Giovanna De Luca, Rome; Giovanni Di Stazio, Rome; Vincenzo Politi, Rome, all of Italy

[73] Assignees: Eniricerche, S.p.A., Milan; Polifarma, S.p.A., Rome, both of Italy

[21] Appl. No.: 246,763

[22] Filed: Sep. 20, 1988

Related U.S. Application Data

[63] Continuation of Ser. No. 870,163, Jun. 3, 1986, abandoned.

[30] Foreign Application Priority Data

Jun. 5, 1985 [IT] Italy .................. 21042 A/85

[51] Int. Cl.$^5$ .................. A61K 37/02; C07K 5/08
[52] U.S. Cl. .................. 514/18; 530/331; 530/330; 530/800
[58] Field of Search .................. 530/331, 330, 800

[56] References Cited

U.S. PATENT DOCUMENTS

| | | | |
|---|---|---|---|
| 3,821,188 | 6/1974 | McKinley et al. | 530/330 |
| 3,917,578 | 11/1975 | Immer et al. | 530/329 |
| 4,216,209 | 8/1980 | Bellini et al. | 530/330 |
| 4,374,120 | 2/1983 | Soini | 436/546 |
| 4,565,790 | 1/1986 | Hemmila | 436/537 |
| 4,619,916 | 10/1986 | Di Stazio et al. | 530/330 |
| 4,666,888 | 5/1987 | Raddatz et al. | 530/330 |
| 4,713,368 | 12/1987 | Sisto et al. | 530/331 |

FOREIGN PATENT DOCUMENTS 0036713  9/1981  European Pat. Off. .......... 530/331

OTHER PUBLICATIONS

International Review of Science, vol. 6, Organic Chemistry Series Two, pp. 140-141, (edited by) Rydon.
Analytical Biochemistry 137, 335-343 (1984)–Hemmila et al., "Europium as a Label in Time-Resolved Immunofluorometric Assays".

Primary Examiner—John Doll
Assistant Examiner—T. D. Wessendorf
Attorney, Agent, or Firm—Hedman, Gibson, Costigan & Hoare

[57] ABSTRACT

Tripeptides having hypotensive activity, defined by the following general formula:

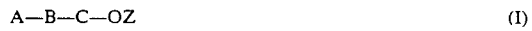

wherein:

A represents a residue of L-pyroglutamic acid, L-proline of L-proline bearing a substituent on its amino group

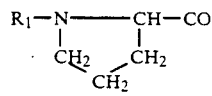

wherein $R_1$ is an acyl with a number of carbon atoms in straight chain not higher than 9, a benzyloxycarbonyl group or an alkyloxycarbonyl group;

B is an α-aminoacide residue derived from one of the natural aminoacids;

C is a residue of L-tryptophan (Trp), of L-phenylalanine (Phe) or of L-tyrosine (Tyr);

Z is a hydrogen atom or an alkyl group with a number of carbon atoms in straight chain not higher than 9.

15 Claims, No Drawings

TRIPEPTIDE COMPOUNDS HAVING HYPOTENSIVE ACTIVITY

This is a continuation application of U.S. patent application Ser. No. 870,163, filed June 3, 1986 now abandoned.

The present invention relates to novel tripeptides having hypotensive activity, useful for the management of the hypertensive states.

From the technical and patent literature peptides having a considerable hypotensive activity on animals and on man are known.

European Patent Appln. Publ. Nr. 0148133, in the name of Polifarma, discloses a class of tripeptides having hypotensive action, characterized in that the N-terminal α-aminoacid is pyroglutamic acid (Glp), and the C-terminal α-aminoacid is L-tryptophan (Trp), whilst the second aminoacid is selected from those present in nature. To the purpose of obtaining novel tripeptidic compounds provided with pharmacological activity, we have modified the aminoacidic sequence of the tripeptide known, by replacing, either contemporaneously or separately, L-pyroglutamic acid with L-proline or L-proline bearing a substituent group on its amino group, and L-tryptophan with L-phenylalanine or L-tyrosine.

By so doing, tripeptides have been synthetized where in the N-terminal α-aminoacid is an L-proline (Pro), an L-proline (Pro.R) bearing a substituent group on its amino group, or pyroglutamic acid (Glp); and the C-terminal α-aminoacid is an L-phenylalanine (Phe), L-tyrosine (Tyr) or L-tryptophan (Trp), and with the limitation that, when the N-terminal α-aminoacid is Glp, the C-terminal α-aminoacid is different from L-tryptophan, and when the C-terminal α-aminoacid is L-tryptophan, the N-terminal one is different from Glp.

The compounds so synthetized have been analyzed in order to verify the relationship between the aminoacid structure of the tripeptide and the presence of a biological activity.

Accordingly, the purpose of the present invention is to provide novel tripeptides having hypotensive activity defined by the following general formula:

$$A—B—C—OZ \qquad (I)$$

wherein:

A represents a residue of L-pyroglutamic acid, L-proline or L-proline bearing a substituent on its amino group $$R_1-N\underset{\underset{CH_2}{CH_2}}{\overset{\phantom{CH_2}}{\diagdown}}\overset{\phantom{CH_2}}{\diagup}CH-CO$$

wherein $R_1$ is an acyl having a number of carbon atoms in straight chain not higher than 9, a benzyloxycarbonyl group or an alkyloxycarbonyl group;

B is an α-aminoacid residue derived from one of natural L-aminoacids;

C is a residue of L-tryptophan (Trp), of L-phenylalanine (Phe) or of L-tyrosine (Tyr);

Z is a hydrogen atom or an alkyl group with a number of carbon atoms in straight chain not higher than 9.

A preferred group of compounds of the present invention comprises those compounds of formula (I) wherein A, C and Z are as previously defined, and B is a residue of an α-aminoacid derived from one of the following aminoacids ids from natural sources: glycine, alanine, valine, leucine, isoleucine, serine, threonine, asparagine, glutamine, arginine, phenylalanine and tyrosine.

The tripeptides (I) of the present invention are synthetized, according to known techniques, in solid phase, by using a polymeric matrix insoluble and swelling in the reaction medium, onto which the individual aminoacids are linked according to the desired sequence.

The tripeptide thus formed is then separated from the resin by treatment by a suitable reactant.

In particular, the polymer used for the synthesis of the tripeptides of the present invention is constituted by small spheres of polyamidic resin suitably functionalized with residues of substituted benzyl alcohol according to the method by R. Arshady et al. [J. Chem. Soc. Perkin I 529 (1981)].

The resin is then activated by treatment with 1,2-diaminoethane and is reacted with fluorenylmethoxycarbonyl-norleucine (Fmoc-NLeu)$_2$O; Fmoc is removed by treatment with piperidine in dimethylformamide and is finally submitted to acylation by 2,4,5-trichlorophenol p-hydroxymethylphenoxyacetate.

The suitably protected aminoacids are activated to symmetrical anhydride before being linked to the modified resin.

In particular, the synthesis is carried out by reacting the protected aminoacid with N,N'-dicyclohexylcarboodiimide, in methylene chloride, at a temperature of 20°–25° C. for a time of about ten minutes. At the end, the precipitated dicyclohexylurea is filtered off from the reaction mixture, the organic solvent is evaporated off, and the symmetrical anhydride formed is separated.

The protective groups suitable to the purpose are selected from those known in the art. In particular, for the α-amino group, as the protecting group fluorenylmethoxycarbonyl is selected, whilst for the groups possibly present in side chain, groups based on tert.butyl are selected; hence, tert.butyl ester for the carboxy functions, tert.butoxycarbonyl for the aminic functions, and tert.butyl ethers for the hydroxy functions.

The first aminoacid residue, activated to symmetrical anhydride, is linked to the resin by forming an ester bond with the substituted benzyl residue.

The residue of substituted benzyl alcohol is selected in such a way that, by treatment with trifluoroacetic acid, at the end of the synthesis the separation of the peptide from the resin may be obtained with high yields.

It is known however that aminoacid residues having an aromatic function of phenolic or indolic type on branched chain undergo, during the acidolytic removal with trifluoroacetic acid, an electrophile attack on the aromatic ring by the benzylic carbocation produced. Such a reaction causes unavoidingly a decrease in yield during the step of peptide separation from the resin.

It has been hence found that overcoming this drawback is possible, by using, during the end step of separation from the resin of the peptide containing residues with aromatic side chains in C-terminal position, ethanedithiol mixed with trifluoroacetic acid, with a volume ratio of 1:9 between the two compounds. At the end of the removal reaction, the resin is filtered off from the reaction mixture and the peptide-containing solution is freeze-dried, a fluffy, colourless residue being obtained.

The desired peptide is then isolated from said residue with yields of from 53% to 78% by reverse-phase high pressure preparative chromatography, using Lichroprep RP-18 20 –40 μm (Merck) as the solid phase, and an aqueous mixture of $CH_3CN$ and trifluoroacetic acid as the eluant.

The identity of tripeptides is confirmed by protonic magnetic resonance spectroscopic analysis ($^1$H-N.M.R.). The purity of the compounds synthetized is tested by reverse-phase high pressure liquid chromatographic analysis (RP-HPLC), using a Perkin Elmer chromatograph with Hibar® column of 250×4 mm, with packing of Lichrosorb® RP-18 10 μm (Merck) and, as the moving phase, an (A) mixture of 90% of $CH_3CN$ and 0.1% trifluoroacetic acid L. (TFA) in water, and a (B) mixture of 10% of $CH_3CN$, and 0.1% of TFA in water.

An elution with linear gradient from 20% of A to 65% of A over a 25-minutes time has been used. The purity of tripeptides synthetized is furthermore checked by thinlayer chromatography (TLC) on silica gel, using the following eluant systems: n-butanol:acetic acid:water (4:1:1) (BWA) and chloroform:methanol:acetic acid (85:10:5) (CMA).

The hypotensive action of the tripeptides of the present invention has been tested on the arterial pressure of normotensive male rats of C.D. strain, available from Charles River Co., of weight of 200–300 g.

The rats have been anaesthetized by ethyl urethane (1.75 g/kg by intraperitoneal way), and, after tracheal cannulating, the right-hand carotid artery has been isolated and connected by cannula to a Hewlett-Packard Model pressure transducer.

From isolated left-hand carotid artery the arterial flow has been recorded by means of the Biotronex® electromagnetic flowmeter Model BL 610.

On Hewlett-Packard Model 8824-C polygraph, the pressure variation with time (dp/dt), the electrocardiogram (ECG) and the beats per minute (BPM) have been recorded. The so tested compounds cause a gradual and long-lasting hypotensive effect which reaches, at the dose of 0.2 mg/kg, a delta for diastolic arterial pressure of from 30 $mm_{Hg}$ to 35 mm and$_{Hg}$ of from 30 $mm_{Hg}$ to 40 $mm_{Hg}$ for the systolic arterial pressure.

Pharmaceutical compositions useful for the management of hypertension will comprise a pharmaceutically acceptable support and a therapeutically effective amount of the tripeptide of the invention. The pharmaceutical compositions may be administered to hypertensive mammals in therapeutically effective amounts.

It has been furthermore found that the daily dose per kg of body weight, referred to the pure compound, is preferably the following: from 2 to 10 mg by intravenous way; from 10 to 50 mg by intramuscular way; and from 100 to 300 mg by oral way.

The purpose of the invention shall be clearer after the reading of the following Examples, which are merely illustrative and in no way must be considered as limitative of the same invention.

EXAMPLE 1

Synthesis of
L-pyroglutamyl-L-asparaginyl-L-phenyl-alanine
(Glp—Asn—Phe—OH)

1 g of polymeric support, constituted by small spheres of polydimethylamide-co-acryloylsarcosine methylester crosslinked with N,N'-ethylene-bis-acrylamide is activated by treatment with 1,2-diaminoethane.

The so-activated resin is reacted with 1.8 mmol of N-fluorenylmethoxycarbonylnorleucine anhydride (Fmoc N—le)$_2$O and is then, after removal of Fmoc by treatment with piperidine at 20% in dimethylformamide (DMF), acylated with 1.8 mmol of 2,4,5-trichlorophenol p-hydroxymethylphenoxyacetate.

The resin so modified contains eventually 0.525 mmol of norleucine (Nle) per gram of resin.

1.39 g (1.8 mmol) of symmetrical anhydride of N-fluorenylmethoxycarbonyl-L-phenylalanine (Fmoc-Phe)$_2$O dissolved in 16 ml of dimethylformamide is treated for 30 minutes with the modified resin, in the presence of 0.2 ml (1.8 mmol) of N-methylmorpholine and 0.022 g (0.18 mmol) of 4-dimethylaminopyridine.

The subsequent aminoacids are sequentially introduced on the modified resin as p-nitrophenol ester of L-N-fluorenylmethoxycarbonylasparagine (Fmoc—Asn—ONP), 0.855 g (1.8 mmol), and pentachlorophenol ester of L-pyroglutamic acid (Glp—OPCP), 0.703 g (1,8 mmol), following the procedure 2 reported in Table 1.

The synthesis of the whole tripeptide is carried out inside the reaction vessel of a Beckman Model 990B automatic synthetizer.

The symmetrical anhydrides of protected aminoacids are preliminarily formed at the acylation time.

3.6 mmol of protected aminoacid is reacted with 1.8 mmol of N,N'-dicyclohexylcarbodiimide in $CH_2Cl_2$, for 10 minutes, at room temperature (20°–25° C.).

At the end of the reaction, the dicyclohexylurea formed is filtered off, $CH_2Cl_2$ is evaporated off under vacuum and the symmetrical anhydride is dissolved in 16 ml of DMF.

For each acylation, the completion of the formation of the amide bond is verified by reacting a resin sample with ninhydrin according to the E. Kaiser's method Anal. Biochem. 34 595 (1970)].

The analyses of the aminoacids are carried out on samples hydrolyzed at 110° C., for 18 hours with HCl at constant boiling temperature, in the presence of phenol, inside ampuls sealed under vacuum.

After the addition of the third aminoacid, the resin is washed with ethyl ether (100 ml), is dried and then suspended in 50 ml of trifluoroacetic acid/ethanedithiol (90/10, v/v) mixture, for 3 hours.

At the end of said time period, the resin is filtered off from the reaction mixture, it is washed with 50 ml of 2N acetic acid and the solution containing the tripeptide is then freeze-dried.

The fluffy and colourless residue thus obtained is chromatographed by using a Miniprep preparative chromatograph of Jobin-Yvon Co., with the solid phase being constituted by 35 g of Lichroprep RP-18 20-40 μm (Merck), using a mixture of 15% of $CH_3CN$, and 0.1% of trifluoroacetic acid in water as the eluant.

The fractions containing the desired product are combined, reduced in volume, and freeze-dried.

110 mg is obtained of tripeptide Glp—Asn—Phe—OH (yield 53%, calculated on the amount of norleucine present on the resin).

On TLC and HPLC analyses the product does not show traces of impurities, and the $^1$H-N.M.R. spectrum confirms its molecular structure.

TLC (CMA) $R_1$:0.18.
(BWA) $R_f$:0.27.
HPLC $t_r$:2.41. minutes

N.M.R.: δ 1.8–2.25 (4H, CH₂ Glp), 3.0 (m 2H, CH₂ Phe), 4.05 (m 1H, CH Glp), 4.25–4.70 (2H, CH Phe, CH Asn), 6.85–7.15 (2H, NH₂-Asn), 7.25 (s. 5H, O), 7.75 (s. 1H, NH Glp), 7.85–8.20 (2H, NH—Phe, NH—Asn).

Solvent: Deuterodimethylsulphoxide.

EXAMPLE 2

Synthesis of Pyroglutamyl-Leucyl-Phenylalanine (Glp—Leu—Phe—OH)

This synthesis is begun as in foregoing Example 1, a modified resin with a content of 0.7 mmol of norleucine per gram of resin being obtained.

The first aminoacid (Phe) and the third aminoacid (Glp) are introduced by following the procedure reported in Example 1, whilst the second aminoacid (leucine) is introduced as its N*-fluorenylmethoxycarbonyl derivative, by using the procedure 1 of Table 1.

At the end of the synthesis, the product is isolated by reverse-phase preparative chromatography, by using 23% of CH₃ CN and 0.1% of trifluoroacetic acid in water as the eluant.

215 mg of tripeptide Glp—Leu—Phe—OH (78%) is obtained.

The product does not show traces of impurities on TLC and HPLC analyses, and the ¹H-N.M.R. spectrum confirms its molecular structure.

TLC (CMA) R_f:0.22.

(BWA) R_f:0.41.

HPLC t_r:6.43 minutes.

N.M.R.: δ —0.82 (q. 6H, CH₃ Leu), 1.20–2.30 (7H, CH₂ Leu, CH Leu, CH₂ Glp), 3.0 (m. 2H, CH₂ Phe), 4.07 (m. 1H, CH Glp), 4.20–4.55 (2H, CH Phe, CH Leu), 7.22 (s. 5H, O), 7.75 (s. 1H, NH Glp), 7.83–8.20 (2H, —NH Phe, NH Leu).

Solvent: Deuterodimethylsulphoxide.

EXAMPLE 3

Synthesis of Prolyl-Leucyl-Triptophan (Pro—Leu—Trp—OH)

0.5 g of resin functionalized up to the benzyl residue as reported in Example 1 is used. Titre in norleucine: 0.7 mmol/g of resin.

The ester bond between L-tryptophan and the resin is realized by treating for a 30 minutes time the modified resin with 0.767 g (0.9 mmol) of symmetrical anhydride of Nα-fluorenyl-methoxycarbonyl-L-tryptophan (FmocTrp)₂O, dissolved in 8 ml of dimethylformamide, in the presence of 0.1 ml (0.9 mmol) of N-methylmorpholine and (0.09 mmol) of L-dimethylaminopyridine.

Leucine is condensed as its Nα-fluorenylmethoxycarbonyl derivative, according to procedure 1 of Table 1.

Pyroglutamic acid is assembled on the resin as its pentachlorophenyl ester by using the procedure 2 of Table 1.

The peptide is removed from the resin according to the procedure as reported in Example 1 and is isolated by preparative chromatography, using CH₃ CN at 27%, and trifluoroacetic acid at 0.1% in water as the eluant.

95 mg of peptide (yield 65%) is obtained. The product does not show traces of impurities on chromatographic (TLC and HPLC) analyses, and the ¹H-N.M.R. spectrum confirms its molecular structure.

TLC (CMA) R_f:0.1.

(BWA) R_f:0.5.

HPLC t_r:8 minutes.

N.M.R.: δ —0.88 (q. 6H, CH₃ Leu), 1.20–2.18 (7H, CH₂ Leu, CH₂ Pro, CH Leu), 3.0–3.60 (4H, CH₂ Trp, CH₂—Pro), 3.85–4.55 (3H, CH Pro, CH Leu, CH Trp), 6.95–7.55 (5H, RING PROTONS), 7.90–8.10 (2H, NH Leu, NH Trp), 10.80 (s. 1H, NH-RING).

Solvent: Deuterodimethylsulphoxide.

EXAMPLE 4

Synthesis of Pyroglutamyl-Glycyl-Phenylalanine (Glp—Gly—Phe—OH)

The peptide is synthetized by using 0.5 g of resin and by using as the derivatives of the aminoacids: Nα-fluorenylmethoxycarbonylphenylalanine (Fmoc-Phe) assembled according to procedure 1, Nα-fluorenylmethoxycarbonylglycine (Fmoc-Gly) (procedure 1), pyroglutamic acid pentachlorophenol ester (procedure 2).

At the end of the assemblage procedures, the peptide is separated from the resin, and isolated by reversephase preparative chromatography, using CH₃ CN at 20% and TFA at 0.1% in water as the eluant phase.

85 mg of fluffy colourless product is obtained (yield 71%). The product does not show traces of impurities on TLC and HPLC analyses, and the ¹H-N.M.R. spectrum confirms its molecular structure.

TLC-(CMA), R_f:0.15.

(BWA) R_f:0.41.

HPLC t_r:2.6 minutes.

N.M.R.: δ —1.80–2.28 (4H, CH₂ Glp), 3.0 (m. 2H, CH₂ Phe), 3.72 (m. CH₂ Gly), 4.07 (m. 1H, CH Glp), 4.45 (m. 1H, CH Phe), 7.25 (s. 5H, O), 7.78 (s. 1H, NH Gly), 7.95–8.30 (2H, NH—Gly, NH—Phe).

Solvent: Deuterodimethylsulphoxide.

EXAMPLE 5

Synthesis of Pyroglutamyl-Leucyl-Tyrosine (Glp—Leu—Tyr—OH)

The peptide is synthetized by using 0.5 g of high-load resin functionalized up to the benzyl residue.

As the derivatives of the aminoacids: Nα-fluorenylmethoxycarbonyl-O-tert.butyl-tyrosine (FmocTyr(Bu^t)OH) (procedure 1, Table 1), FmocLeu (procedure 1, Table 1), and GlpOPCP (procedure 2, Table 1) are used.

At the end of the procedures of peptide assemblage and separation from the resin, the product is isolated by reverse-phase preparative chromatography, by using 11% of CH₃ CN and 0.1% of TFA in water as the eluant phase.

111 mg of fluffy colourless product is obtained (yield 67%).

The product does not show traces of impurities on chromatographic (TLC and HPLC) analyses, and the ¹H-N.M.R. spectrum confirms its molecular structure.

TLC (CMA) R_f:0.25.

(BWA) R_f:0.34.

HPLC t_r:3.02 minutes

N.M.R.: δ —0.85 (q. 6H, CH₃ Leu), 1.18–2.23 (7H, CH-Leu, CH₂ Glp), 2.90 (m. 2H, CH₂ Tyr), 4.0 (m. 1H, CH Glp), 4.18–4.26 (2H, CH Leu, CH Tyr), 6.50–7.10 (4H, 0), 7.75 (s. 1H, NH Glp), 7.80–8.10 (2H, NH Leu, NH Tyr) , 2.10 (1. broad, 1H, OH Tyr).

Solvent: Deuterodimethylsulphoxide.

TABLE 1

PROCEDURES USED IN THE SYNTHESIS IN SOLID PHASE

| Procedure 1 | Procedure 2 |
|---|---|
| (1) 5 washings with DMF | (1) 5 washings with DMF |
| (2) 2 treatments with piperidine at 20% in DMF | (2) 2 treatments with piperidine at 20% in DMF |
| (3) 10 washings with DMF | (3) 10 washings with DMF |
| (4) Acylation via symmetrycal anhydride | (4) Acylation with dicyclohexylcarbodiimide and N-hydroxybenzotriazole |
| (5) 5 washings with DMF | (5) 5 washings with DMF |

We claim:

1. A tripeptide which is L-pyroglutamyl-L-asparaginyl-L-phenylalanine.

2. A tripeptide which is pyroglutamylleucyl-phenylalanine.

3. A tripeptide which is prolyl-leucyltryptophan.

4. A tripeptide which is pyroglutamylglycyl-phenylalanine.

5. A tripeptide which is pyroglutamyl-L-leucyl-tyrosine.

6. A method for reducing blood pressure in mammals which comprises administering to a mammal a therapeutically effective amount of the peptide of claim 1.

7. A method for reducing blood pressure in mammals which comprises administering to a mammal a therapeutically effective amount of the peptide of claim 2.

8. A method for reducing blood pressure in mammals which comprises administering to a mammal a therapeutically effective amount of the peptide of claim 3.

9. A method for reducing blood pressure in mammals which comprises administering to a mammal a therapeutically effective amount of the peptide of claim 4.

10. A method for reducing blood pressure in mammals which comprises administering to a mammal a therapeutically effective amount of the peptide of claim 5.

11. A pharmaceutical composition having antihypertensive activity which consists essentially of the peptide of claim 1 and a pharmaceutically acceptable support.

12. A pharmaceutical composition having antihypertensive activity which consists essentially of the peptide of claim 2 and a pharmaceutically acceptable support.

13. A pharmaceutical composition having antihypertensive activity which consists essentially of the peptide of claim 3 and a pharmaceutically acceptable support.

14. A pharmaceutical composition having antihypertensive activity which consists essentially of the peptide of claim 4 and a pharmaceutically acceptable support.

15. A pharmaceutical composition having antihypertensive activity which consists essentially of the peptide of claim 5 and a pharmaceutically acceptable support.

* * * * *